(12) United States Patent
Hara et al.

(10) Patent No.: US 8,138,359 B2
(45) Date of Patent: Mar. 20, 2012

(54) STABILIZED 3-HYDROXYFLAVAN COMPOSITIONS AND METHODS THEREFOR

(75) Inventors: Yukihiko Hara, Tokyo (JP); Hiroshi Hojo, Shizuoka (JP); Slobodan Jovanovic, Nepean (CA)

(73) Assignee: Mitsui Norin Co., Ltd., Tokyo (JP)

( * ) Notice: Subject to any disclaimer, the term of this patent is extended or adjusted under 35 U.S.C. 154(b) by 911 days.

(21) Appl. No.: 11/996,933

(22) PCT Filed: Jul. 26, 2005

(86) PCT No.: PCT/US2005/026521
§ 371 (c)(1),
(2), (4) Date: Jul. 21, 2008

(87) PCT Pub. No.: WO2007/018502
PCT Pub. Date: Feb. 15, 2007

(65) Prior Publication Data
US 2008/0300302 A1  Dec. 4, 2008

(51) Int. Cl.
*C07D 311/62* (2006.01)
*C07F 9/50* (2006.01)
(52) U.S. Cl. .................................. 549/399; 549/220
(58) Field of Classification Search .............. 549/399, 549/220
See application file for complete search history.

(56) References Cited

U.S. PATENT DOCUMENTS
6,299,925 B1   10/2001   Xiang
2003/0170319 A1   9/2003   Netke
2004/0063648 A1   4/2004   Pandol

FOREIGN PATENT DOCUMENTS
JP   7-238079   9/1995

OTHER PUBLICATIONS

Richard-Forget, Florence, Isolation and characterization of a "quinone-trapping" substance from a crude Carica papaya protein preparation, International Journal of Food Science and Technology, 1998, 33, 285-296, Blackwell Science Ltd.

Tanaka, Takashi, Synthesis of Theaflavin from Epicatechin and Epigallocatechin by Plant Homogenates and Role of Epicatechin Quinone in the Synthesis and Degradation of Theaflavin, Journal of Agricultural and Food Chemistry, 2002, 50, 2142-2148, American Chemical Society.

Moridani, Majid Y., Catechin Metabolism: Glutathione Conjugate Formation Catalyzed by Tyrosinase, Peroxidase, and Cytochrome P450, Chem. Res. Txoicol. 2001, 14, 841-848, American Chemical Society.

Sang, Shengmin, Synthesis and Structure Identification of Thiol Conjugates of (−) Epigallocatechin Gallate and Their Urinary Levels in Mice, Chem. Res. Toxicol., 2005, 18, 1762-1769, American Chemical Society.

Moridani, Majid Y., Caffeic acid, chlorogenic acid, and dihydrocaffeic acid metabolism: glutathione conjugate formation, Drug Metabolism and Disposition, 2001, vol. 29, No. 11, 1432-1439, The American society for Pharmacology and Experimental Therapeutics.

Richard-Forget, Florence C., Cysteine as an Inhibitor of Enzymatic Browning. 2. Kinetic Studies, Journal of Agricultural and Food Chemistry, 1992, 40, 2108-2113, American Chemical Society.

Richard, Florence C., Cysteine as an Inhibitor of Enzymatic Browning. 1. Isolation and Characterization of Addition Compounds Formed during Oxidation of Phenolics by Apply Polyphenol Oxidase, Journal of Agricultural and Food Chemistry, 1991, 38, 841-847, American Chemical Society.

Yasuda, Hideyuki, Deodorizing Mechanism of (−)-Epigallocatechin Gallate against Methyl Mercaptan, Biosci., Biotech., Biochem., 1995, 59 (7), 1232-1236.

Roberts, E.A.H., The Interaction of Flavanol Orthoquinones with Cysteine and Glutathione, Chemistry and Industry, Aug. 1, 1959.

Richard-Forget, F., Kinetic Studies on Inhibition of Enzymatic Browning by Cysteine, Bull. Liasioin—Groupe Polyphenols, 1992, pp. 205-212.

Negishi, Osamu, et al. "Inhibition of Enzymatic browning and protection of sulfhydryl enzymes by thiol compounds." Institute of Applied Biochemistry, University of Tsukuba, Tsukuba, ibaraki 305-8572, Japan. Jul. 27, 2000. pp. 1-16.

*Primary Examiner* — Bernard Dentz
(74) *Attorney, Agent, or Firm* — Fish & Associates, PC

(57) ABSTRACT

Compositions and methods are directed to covalent adducts between reducing agents and optionally substituted 3-hydroxyflavans, wherein the reducing agent is covalently bound to the B-ring of the 3-hydroxyflavan. Such adducts exhibit markedly increased stability towards oxidation as compared to the unmodified 3-hydroxyflavan. Particularly preferred 3-hydroxyflavans include green tea catechins, and especially EGCG, while especially preferred reducing agents include NAC and glutathione.

13 Claims, 2 Drawing Sheets

STABILIZED 3-HYDROXYFLAVAN COMPOSITIONS AND METHODS THEREFOR

FIELD OF THE INVENTION

Compositions and methods for chemically modified catechins and catechin-containing compositions, especially as they relate to stabilized catechins and compositions.

BACKGROUND OF THE INVENTION

Catechins, and particularly green tea catechins are well known in numerous uses for improving health. For example, many nutritional supplements and cosmetic formulations comprise catechins and other allegedly active ingredients, including various antioxidants, minerals, vitamins, etc. Unfortunately, most catechins, and especially epigallocatechin gallate (EGCG) are relatively unstable and tend to oxidize rapidly. Worse yet, oxidation is typically exacerbated in aqueous environment in the presence of metal ions.

Not surprisingly, numerous strategies have been reported to reduce EGCG oxidation using various strategies. For example, compositions may be formulated in the absence of oxygen. Alternatively, EGCG oxidation may be delayed by providing sacrificial compounds and/or anti-oxidants to the formulations. Antioxidants have also been combined with EGCG for other purposes, and especially to provide reduction of oxidative stress in patients that are also treated with EGCG. For example, EGCG is combined with NAC as described in U.S. Pat. App. Nos. 2003/0170319 and 2004/0063648 in formulations to treat cancer. In U.S. Pat. No. 6,299,925, EGCG is combined with NAC in an effervescent drink, while the same combination is taught in GB2385768 for animal feed. While such known combinations at least sometimes provide beneficial effects, EGCG concentrations in such composition often rapidly decline due to autoxidation or other oxidative processes. Selected cysteine conjugates with catechins were described in WO 03/024951, in which cysteine was covalently reacted with the C-ring in 4-position to form an antioxidant with increased antioxidative properties. While such conjugates may provide at least some advantages, various disadvantages nevertheless remain. Among other things, as the adduct is formed on the C-ring in 4-position, such adducts are generally not available for gallate esters of catechins (e.g., EGCG). Furthermore, such modifications will introduce a net charge into the molecule in many environments, and thereby tend to prevent passive transmembrane transport.

Therefore, while numerous compositions and methods for catechins and catechin-containing compositions are known in the art, all or almost all of them, suffer from one or more disadvantage. Thus, there is still a need for stabilized catechin compositions and methods therefor.

SUMMARY OF THE INVENTION

The present invention is directed to compositions and methods of reducing catechin oxidation wherein a composition comprises an isolated 3-hydroxyflavan adduct in which a reducing agent is covalently bound to a B-ring of the 3-hydroxyflavan. Most preferably, the 3-hydroxyflavan is (−)-Epigallocatechin gallate (EGCG), (−)-Gallocatechin gallate (GCG), (+)-Epigallocatechin gallate, (+)-Gallocatechin gallate, (−)-Epigallocatechin (EGC), (−)-Gallocatechin (GC), (+)-Epigallocatechin, (+)-Gallocatechin, (−)-Epicatechin gallate (ECG), (−)-Catechin gallate (CG), (+)-Epicatechin gallate, (+)-Catechin gallate, (−)-Epicatechin (EC), (−)-Catechin (C), (+)-Epicatechin and/or (+)-Catechin. It is also preferred that the reducing agent in such compositions is covalently bound via a sulfur atom to a carbon atom of the B-ring.

In further preferred aspects, the reducing agent is a nutritionally acceptable reducing agent (N-acetyl cysteine). Alternatively, or additionally, suitable reducing agents may also include various N-substituted cysteines, glutathione, dithiothreitol (DTT), dithioerytlirol (DTE), mercaptoethanol, and/or Tris(2-carboxyethyl)phosphine (TCEP). Most preferably, the pH of contemplated compositions is neutral to acidic, and typically between pH between 4.0 and 6.0, inclusive.

Thus, and viewed from a different perspective, preferred 3-hydroxyflavan adducts will have a structure according to Formula I (Rings are identified with A, B, and C):

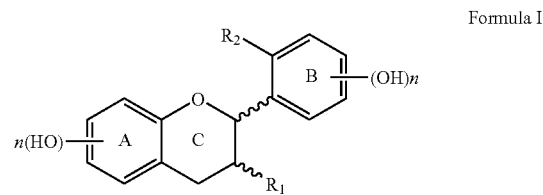

Formula I in which n is independently between 0 and 3, inclusive; $R_1$ is selected from H, OH, an optionally substituted aryl ester, an optionally substituted aryl thioester, and an optionally substituted aryl amide; and in which $R_2$ is a reducing agent that is covalently bound via a sulfur atom to the carbon atom of the B-ring. Consequently, the term "3-hydroxyflavan" as used herein expressly includes compounds with a 3-OH group and a substituted 3-OH group (e.g., in which the OH group is esterified with a substituted benzoic acid [e.g., Gallic acid]).

Most preferably, $R_1$ and $R_2$, have a structure according to Formula II and Formula III, respectively,

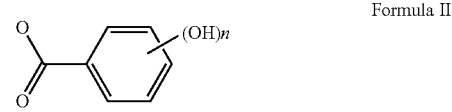

Formula II

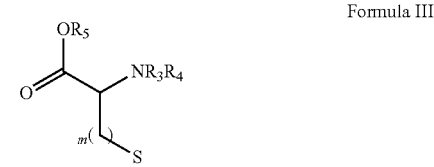

Formula III wherein n is between 0 and 3, inclusive, and wherein $R_3$, $R_4$, and $R_5$ are independently selected from the group consisting of H, acyl, alkyl, aryl, each of which may be substituted, and wherein m is an integer between 1 and 5.

In another aspect of the inventive subject matter, a composition includes a reducing agent in a first quantity, and a 3-hydroxyflavan in a second quantity, wherein the 3-hydroxyflavan has an A-ring and a B-ring, wherein the first quantity is a predetermined function of the second quantity such that the reducing agent is present in an amount effective to reduce discoloration of the composition, wherein the discoloration is due to at least one of an oxidation, a dimerization, a oligomerization, and a polymerization of the 3-hydroxyflavan, and wherein the reducing agent has a structure to allow reaction with an atom in the B-ring of the 3-hydroxy-flavan to form a covalent adduct to thereby reduce the discoloration.

Most typically, the reducing agent is present in such compositions in at least stoichiometric quantity relative to the 3-hydroxyflavan, and the composition is a cosmetic formulation for topical administration to skin or a nutritional formulation for enteral administration to a mammal. Alternatively, contemplated compositions may also be an intermediate in a process for isolation of a 3-hydroxyflavan.

In yet another aspect of the inventive subject matter, a method of reducing discoloration of a 3-hydroxyflavan-containing composition (wherein the discoloration is due to oxidation, dimerization, oligomerization, and/or polymerization of the 3-hydroxyflavan) comprises one step in which the 3-hydroxyflavan is combined with a reducing agent under conditions that allow reaction of the reducing agent with an atom in the B-ring of the 3-hydroxyflavan to form a covalent adduct to thereby reduce the discoloration.

Various objects, features, aspects and advantages of the present invention will become more apparent from the following detailed description of preferred embodiments of the invention, along with the accompanying drawing.

DETAILED DESCRIPTION

Figure 1A:
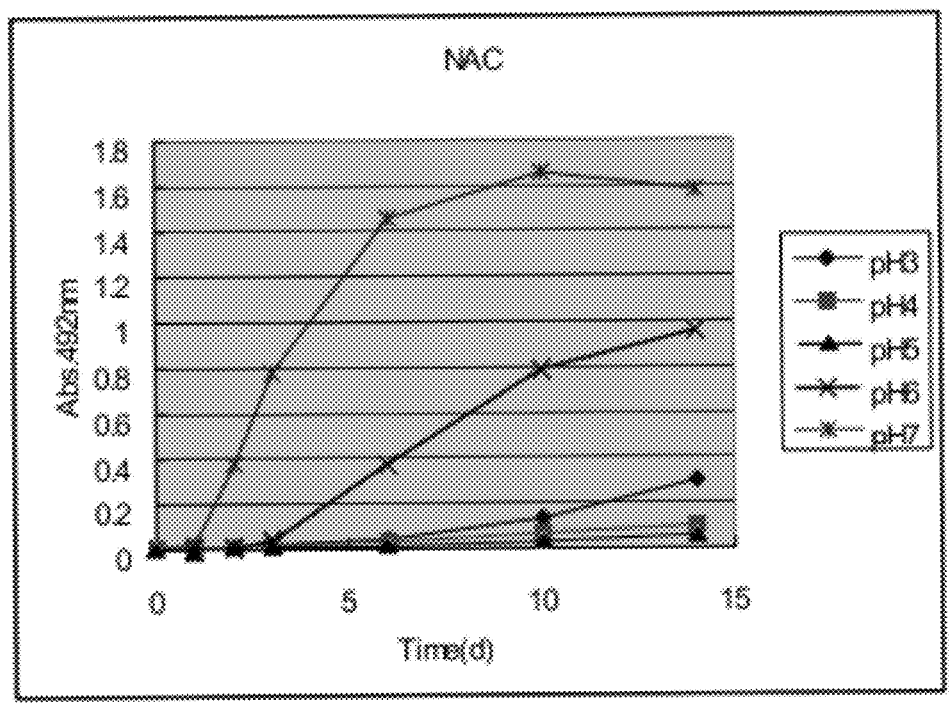
FIG. 1A is a graph depicting color formation of EGCG in aqueous solutions of varying pH over time in the presence of NAC.

The inventors discovered that oxidation of numerous 3-hydroxyflavans, and especially oxidative discoloration of compositions comprising EGCG and other tea catechins can be reduced, and in many instances even entirely avoided where the 3-hydroxyflavan is combined with a reducing agent at a concentration and under conditions effective to form a covalent adduct between the 3-hydroxyflavan and the reducing agent.

Most preferably, contemplated 3-hydroxyflavans include those typically found in plant catechins, and especially in green tea catechins. Therefore, suitable 3-hydroxyflavans may be present in complex mixtures (e.g., polyphenon E or polyphenon B (produced by Mitsui Norin Co., Ltd)), or as isolated compounds (e.g., EGCG). With respect to preferred reducing agents, it is generally contemplated that such agents will be suitable for nutritional, pharmaceutical, and/or topical formulations, Thus, and among other preferred reducing agents, NAC is especially contemplated.

In one exemplary aspect of the inventive subject matter, EGCG is combined with N-acetyl cysteine (NAC) in an aqueous solvent, wherein NAC is present in two-fold molar excess relative to EGCG, which is present at a concentration of about 2 mM. The aqueous solution is buffered with 100 mM phosphate buffer at a pH of 6.5 and the reaction is allowed to proceed for 24 hours at elevated temperature (typically 55-60° C.) to form the products (−)-EGCG-NAC and (−)-GCG-NAC as shown below.

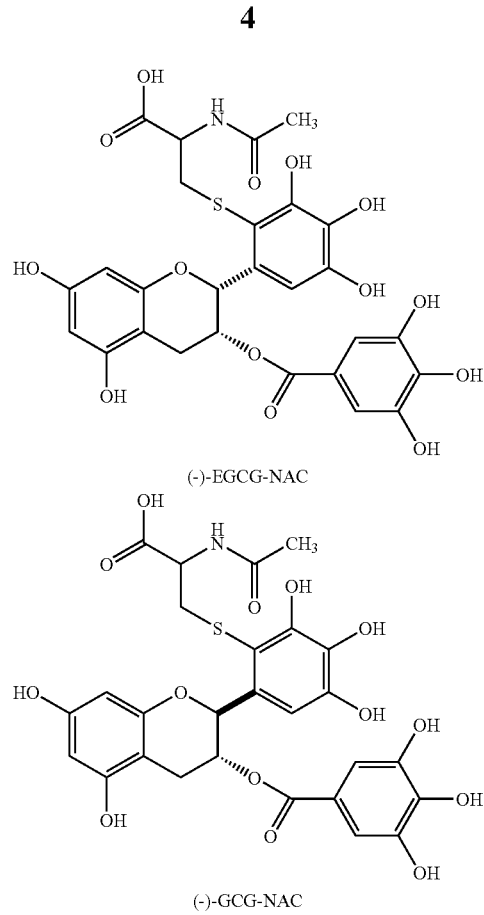

(−)-EGCG-NAC (−)-GCG-NAC

It should be appreciated, however, that numerous alternative 3-hydroxyflavans are also deemed suitable for use herein, and especially preferred 3-hydroxyflavans include (−)-Epigallocatechin gallate, (−)-Gallocatechin gallate, (+)-Epigallocatechin gallate, (+)-Gallocatechin gallate, (−)-Epigallocatechin, (−)-Gallocatechin, (+)-Epigallocatechin, (+)-Gallocatechin, (−)-Epicatechin gallate, (−)-Catechin gallate, (+)-Epicatechin gallate, (+)-Catechin gallate, (−)-Epicatechin, (−)-Catechin, (+)-Epicatechin, and/or (+)-Catechin. Still further preferred 3-hydroxyflavans will generally have a structure according to Formula IV

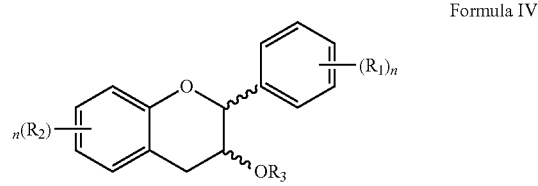

Formula IV in which $R_1$ and $R_2$ are independently H, OH, SH, halogen, alkyl, alkenyl, alkynyl, aryl, O-alkyl, amino radical, amido radical, imino radical, each of which may be optionally substituted, in which $R_3$ is H, optionally substituted aryl ester, an optionally substituted aryl thioester, and an optionally substituted aryl amide, and in which n is independently an integer between 0 and 5. Furthermore, it should be appreciated that contemplated compounds may have one or more chiral centers, and it is noted that all stereochemical configurations and conformations are contemplated herein.

Therefore, in alternative aspects of the inventive subject matter, the 3-hydroxyflavans may be reacted as individual compounds, or in mixtures of two or more 3-hydroxyflavans. For example, where EGCG oxidation is to be prevented, EGCG may be reacted as the sole reactant. On the other hand, where catechin extracts are reacted with the reducing agent(s), complex mixtures (e.g., polyphenon E (produced by Mitsui Norin Co., Ltd)) may be combined with the reducing agent(s). Adducts are expected to be formed depending on the reactivity of the particular 3-hydroxyflavan and reaction conditions chosen.

Preferably, the adduct forming reaction is carried out in an aqueous solvent, which may or may not further include an organic co-solvent (e.g., to increase solubility of one or more components). Alternatively, reactions may also be carried out in an organic solvent, and most typically in an organic solvent that is used to isolate and/or concentrate the catechins (e.g., ethanol, methanol, acetone, DMF, DMSO, carbon dioxide, etc). Typically the reaction is performed at neutral (e.g., pH 6.5 to 7.5) to slightly acidic pH (e.g., pH 4.5 to 6.4), but may also be performed at acidic (e.g., pH of less than 4.5) or basic conditions (e.g., pH of greater than 7.5). Still further, it should be appreciated that suitable reaction conditions may include use of a catalyst, pre-activation of one or more reactants (e.g., deprotonation of thiol group, addition of leaving group into 3-hydroxyflavan, etc.), or other manner that increases yield of the adduct.

With respect to appropriate reaction temperature and duration, it should be recognized that a person of ordinary skill in the art will be readily able to determine optimum conditions (e.g., based on chromatographic analysis of reaction products). However, it is typically preferred that the temperature is between about 20° C. and 70° C., and most preferably between about 40° C. and 60° C. Similarly, it should be recognized that the duration of the reaction may vary considerably, and that the exact duration may depend on numerous factors, including desired yield, reaction temperature, solvents, the reducing agent, etc. Therefore, contemplated reaction temperatures may be between several minutes to several days, or even more. For example, where the temperature is relatively high (e.g., greater than 70° C.) and relatively low yields (e.g., less than 20%) of the adduct are desired, suitable reaction durations may be between 1 and 240 minutes. On the other hand, and especially where relatively high yields (e.g., more than 80%) of the adduct are desired, suitable reaction durations may be between 12 hours and 96 hours (or even longer). Still further, it is contemplated that the reducing agent and the 3-hydroxyflavan may be combined at room temperature (typically about 20° C.) or other temperature without a predetermined time and/or temperature. In such case, it is contemplated that the adduct formation will proceed relatively slowly and may not reach completion over several days or even weeks.

In further preferred aspects, the molar ratio between the 3-hydroxyflavan and the reducing agent is preferably at least stoichiometric, and more preferably, the reducing agent is present in a molar excess relative to the 3-hydroxyflavan. For example, it is contemplated that the molar ratio of reducing agent to 3-hydroxyflavan is at least 1:1.0, more typically at least 1:1.5, even more typically at least 1:2.0, and most typically at least 1:2.5 (or even higher). Consequently, yields of the so formed adducts may vary substantially, and all yields are generally contemplated, including 0-10%, more typically 10-30%, even more typically 30-70%, and most typically 70-99.9%.

With respect to suitable reducing agents, it is generally contemplated that numerous reducing agents known in the art are suitable so long as such reducing agents can react with contemplated 3-hydroxyflavans to form a covalent adduct. However, most typically, reducing agents will include a thiol group, hydroxyl group, or are a phosphine. Furthermore, it is contemplated that the reducing agent may be a single compound, or a mixture of two or more reducing agents. Similarly, it should be recognized that a single (or more) reducing agent may be reacted with a mixture of 3-hydroxyflavans to form the corresponding covalent adducts. In most preferred aspects, the reducing agent is suitable for pharmaceutical, nutraceutical, and/or topical use (e.g., those having an SH group, including N-substituted cysteine, glutathione, dithiothreitol, dithioerythrol, or mercaptoethanol). Thus, the reducing agent is preferably isolated from natural sources. For example, such preferred reducing agents particularly include N-acetyl cysteine isolated from Shiitake. Where NAC is isolated from a natural source (e.g., plant, fungus, bacteria, etc.) it is especially preferred that the 3-hydroxyflavan is also isolated from a natural source (typically green tea). Alternatively, suitable reducing agents may also be synthetic (e.g., Tris(2-carboxyethyl)phosphine, or substituted sulfur, selenium, or oxygen-containing amino acid). Still further contemplated reducing agents include those that are capable of reacting as a nucleophile in an aromatic nucleophilic reaction (e.g., addition or substitution) on the B-ring of contemplated 3-hydroxyflavans.

So formed covalent adducts may be isolated (using at least one step of enrichment), or may be directly used without further workshop. Thus, the adducts may be a pure preparation, which may include selected stereoisomers, enantiomers, etc., or may be a relatively complex mixture, which may or may not further comprise residual reducing agent and/or 3-hydroxyflavan. Contemplated 3-hydroxyflavan adducts may therefore be isolated (i.e., enriched in the adduct using at least one purification step), or be present in a crude reaction mixture.

Consequently, the inventors contemplate a composition that includes an isolated 3-hydroxyflavan adduct in which a reducing agent is covalently bound to a B-ring of the 3-hydroxyflavan. The term "reducing agent is covalently bound to a B-ring" as used herein means that a reducing agent has reacted with an atom of the B-ring. Therefore, in the covalently bound state, the reducing agent may be chemically changed (as compared to the chemical structure of the reducing agent before the reaction) and may therefore also have altered properties with respect to the ability to act as a reducing agent. Such adduct may be present in contemplated composition to varying degree. For example, contemplated compositions may include the adduct in an amount of between about 0.1 wt % to about 2 wt %, more preferably between about 2 wt % to 10 wt %, and most preferably between about 10 wt % and 50 wt % (and even more). An exemplary structure of preferred compounds is depicted in Formula I below

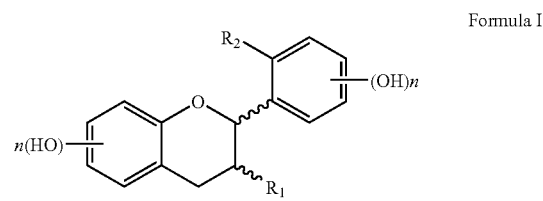

Formula I in which n is independently between 0 and 3, inclusive; $R_1$ is selected from H, an optionally substituted aryl ester, an optionally substituted aryl thioester, and an optionally substituted aryl amide; and $R_2$ is a reducing agent that is covalently bound via a sulfur atom to the carbon atom of the B-ring.

Contemplated covalent adducts and compositions comprising same may be employed in numerous manners, however, particularly preferred manners include incorporation into food products (e.g., nutritional supplements [snack bar, pill, powder, etc.], beverages [soda, green tea, etc.], pet food, etc), cosmetic products (e.g., shampoo, soap, skin cream or lotion, sun screen, etc.), pharmaceutical products (e.g., antineoplastic formulations), etc. Most preferably, such products will have a pH that is neutral to slightly acidic (e.g., between pH 4.0 to 6.0), but alternative pH values are also deemed suitable herein.

Therefore, the inventors also contemplate a composition that comprises a reducing agent in a first quantity, and a 3-hydroxyflavan (having an A-Ring and a B-ring) in a second quantity, wherein the 3-hydroxyflavan, wherein the first quantity is a predetermined function of the second quantity such that the reducing agent is present in an amount effective to reduce discoloration of the composition, wherein the discoloration is due to oxidation, dimerization, oligomerization, and/or polymerization of the 3-hydroxyflavan. In such compositions, it is generally contemplated that the reducing agent has a structure to allow reaction with an atom in the B-ring of the 3-hydroxyflavan to form a covalent adduct to thereby reduce the discoloration. Viewed from another perspective, the inventors contemplate a method of reducing discoloration of a 3-hydroxyflavan-containing composition (discoloration is due to oxidation, dimerization, oligomerization, and/or polymerization of the 3-hydroxyflavan) that includes a step of combining the 3-hydroxyflavan with a reducing agent under conditions that allow reaction of the reducing agent with an atom in the B-ring of the 3-hydroxyflavan to form a covalent adduct to thereby reduce the discoloration.

Experiments

Prevention of Discoloration

Figure 1B:
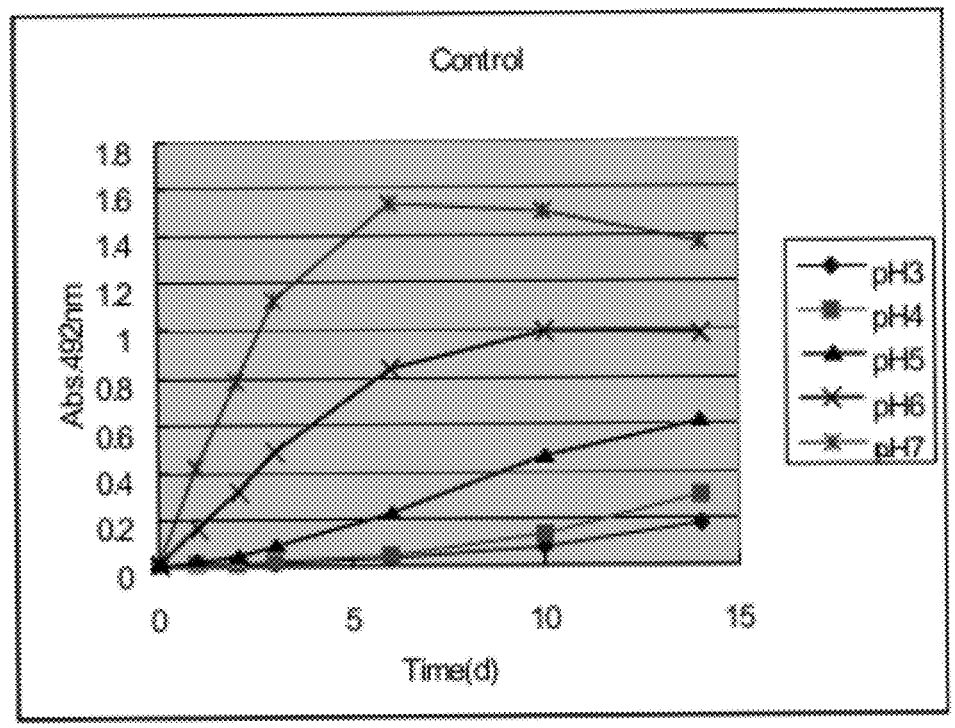
FIG. 1B is a graph depicting color formation of EGCG in aqueous solutions of varying pH over time in the absence of NAC.
Figure 1C:
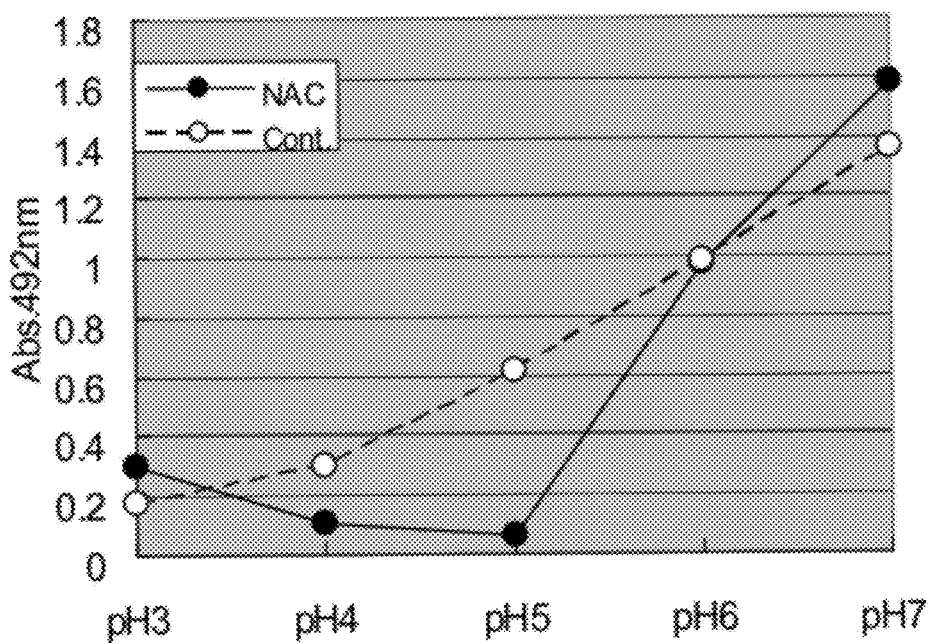
FIG. 1C is a graph depicting color formation as a function of pH of the solvent in the presence and absence of NAC.

In a typical experiment, an aqueous solution of NAC was used in combination with EGCG to demonstrate the stabilization of EGCG over time. Discoloration was measured using a spectrophotometer at a fixed wavelength of 492 nm. More specifically, solutions of EGCG (2 mM) and NAC (4 mM) were prepared in McIlvaine buffer at various pH levels in 1.0 increments between pH 3.0 to pH 7.0. A control experiment was set up without NAC but otherwise identical conditions. The so prepared solutions were incubated at 55° C. and the discoloration was measured at 492 nm over the next 15 days. FIGS. 1A and 1B depict the results in a graph in which discoloration is plotted as a function of time, and in which each of the individual pH values are represented by a respective curve. As can be clearly seen, discoloration is substantially reduced at pH levels of less than 6.0. FIG. 1C depicts the discoloration after 15 days as a function of the pH for both NAC and control. Remarkably, while glutathione and NAC readily reacted to the adducts and prevented discoloration at the observed pH ranges in further experiments (data not shown), cysteine failed to provide significant protection from discoloration.

Isolation and Structure Elucidation of Adducts from EGCG and NAC Reaction

Figure 2:
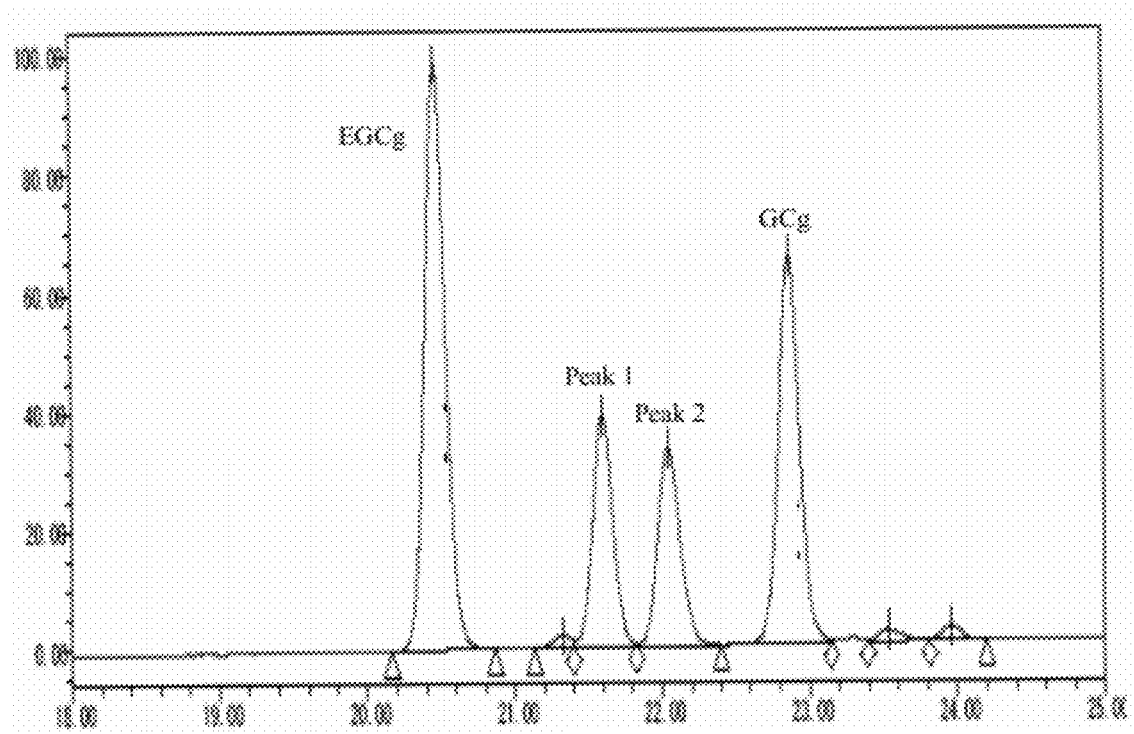
FIG. 2 is a graph depicting an elution profile of a solution in which EGCG was allowed to react with NAC to form covalent adducts.

A reaction was prepared from EGCG (1000 mg; 2.18 mM) and NAC (713 mg; 4.37 mM) in 0.1 M phosphate buffer (pH 6.5) in a volume of 1000 ml. The solution was incubated at 60° C. for 24 hours. After completion of the reaction, HPLC analysis revealed two major products as shown in the elution profile of FIG. 2.

More specifically, the reaction mixture was subjected to DIAION HP-20 column chromatography using a stepped gradient of $H_2O$-MeOH to give adduct fractions (342.5 mg). A portion of that fraction (100 mg) was further fractionated by preparative reversed-phase silica gel column chromatography using a gradient of $H_3PO_4$aq./MeCN. Compounds under peak 1 (11.3 mg) and peak 3 (12.4 mg) ware isolated, and the structure elucidated from NMR experiments using $^1H$, $^{13}C$, H-H COSY, HMBC, NOESY, ROESY. $^1H$ and $^{13}C$-NMR spectra data are shown in the Table below. Each compound had an N-acetyl cysteine attached to the C2' position. The location of the B-ring was assigned as C2 position based on NOESY and ROESY experiments, H3 signal had correlation to H6' at peak 3, although such correlation was not observed for peak 1.

| | Peak 1 | | | | Peak 3 | | | |
|---|---|---|---|---|---|---|---|---|
| | $^{13}$C-NMR (100 MHz, acetone-d 6) | | | | | | | |
| C2 | 76.4 | | | | 77.1 | | | |
| C3 | 68.5 | | | | 69.4 | | | |
| C4 | 27.0 | | | | 26.5 | | | |
| C4a | 99.1 | | | | 99.7 | | | |
| C5 | 157.3 | | | | 156.9 | | | |
| C6 | 96.5 | | | | 96.5 | | | |
| C7 | 157.6 | | | | 157.2 | | | |
| C8 | 95.9 | | | | 95.6 | | | |
| C8a | 157.8 | | | | 158.1 | | | |
| C1' | 134.0 | | | | 133.3 | | | |
| C2' | 108.2 | | | | 111.4 | | | |
| C3' | 148.2 | | | | 148.1 | | | |
| C4' | 133.2 | | | | 133.9 | | | |
| C5' | 147.7 | | | | 147.7 | | | |
| C6' | 108.6 | | | | 107.3 | | | |
| C1" | 121.8 | | | | 121.3 | | | |
| C2" | 110.0 | | | | 109.9 | | | |
| C3" | 145.9 | | | | 146.1 | | | |
| C4" | 138.8 | | | | 139 | | | |
| C5" | 145.9 | | | | 146.1 | | | |
| C6" | 110.0 | | | | 109.9 | | | |
| galbyl-CO | 166.0 | | | | 166.1 | | | |
| CysH α | 53.5 | | | | 53.7 | | | |
| CysH β | 39.9 | | | | 38.6 | | | |
| Acetyl-CH3 | 22.7 | | | | 22.5 | | | |
| Acetyl-CO | 171.2 | | | | 171.8 | | | |
| COOH | 171.9 | | | | 172.3 | | | |
| | $^1$H-NMR (400 MHz, acetone-d 6) | | | | | | | |
| H2 | 5.69 | 1H | brs | | 5.91 | 1H | d | J = 8.2 |
| H3 | 5.68 | 1H | m | | 5.52 | 1H | ddd | J = 5.6, 8.2, 8.2 |
| H4a | 2.95 | 1H | dd | J = 1.8, 17.5 | 2.76 | 1H | dd | J = 8.2, 16.0 |
| H4b | 3.06 | 1H | dd | J = 4.4, 17.5 | 3.18 | 1H | dd | J = 5.6, 16.0 |
| H6 | 6.07 | 1H | d | J = 2.3 | 6.07 | 1H | d | J = 2.4 |
| H8 | 6.05 | 1H | d | J = 2.3 | 5.9 | 1H | d | J = 2.4 |
| H2' | | | | | | | | |
| H6' | 6.9 | 1H | s | | 6.59 | 1H | s | |
| H2", 6" | 6.99 | 2H | s | | 7.06 | 2H | s (br) | |
| Cys-H α | 4.7 | 1H | ddd | J = 4.8, 8.0, 8.2 | 4.64 | 1H | ddd | J = 6.6, 6.6, 7.5 |
| Cys-H β 1 | 3.16 | 1H | dd | J = 8.2, 13.2 | 3.2 | 1H | dd | J = 6.6, 14.0 |
| Cys-H β 2 | 3.23 | 1H | dd | J = 4.8, 13.2 | 3.28 | 1H | dd | J = 6.6, 14.0 |
| N—CH3 | 1.95 | 3H | s | | 1.91 | 3H | s | |
| NH | 7.67 | 1H | d | J = 8.0 | 7.81 | 1H | d | J = 7.5 |

-continued

Peak 1

[Chemical structure labeled Peak-1]

Peak 3

[Chemical structure labeled Peak-3]

Thus, specific embodiments and applications of stabilized catechin compositions and methods therefor have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A composition comprising:
   an isolated 3-hydroxyflavan adduct in which a reducing agent, selected from the group consisting of a N-substituted cysteine, glutathione, dithiothreitol, dithioerythrol, mercaptoethanol, and Tris(2-carboxyethyl)phosphine, is covalently bound to a B-ring of the 3-hydroxyflavan, with the proviso that (a) where the 3-hydroxyflavan is catechin, then the reducing agent is not glutathione or glutamine-cysteine dipeptide;
   (b) where the 3-hydroxyflavan is epicatechin, then the reducing agent is not dithiothreitol or glutamine-cysteine dipeptide.

2. The composition of claim 1 wherein the reducing agent is covalently bound via a sulfur atom to a carbon atom of the B-ring.

3. The composition of claim 1 wherein the reducing agent is a nutritionally acceptable reducing agent.

4. The composition of claim 1 wherein the 3-hydroxyflavan is selected from the group consisting of (−)-Epigallocatechin gallate, (−)-Gallocatechin gallate, (+)-Epigallocatechin gallate, (+)-Gallocatechin gallate, (−)-Epigallocatechin, (−)-Gallocatechin, (+)-Epigallocatechin, (+)-Gallocatechin, (−)-Epicatechin gallate, (−)-Catechin gallate, (+)-Epicatechin gallate, (+)-Catechin gallate, (−)-Epicatechin, (−)-Catechin, (+)-Epicatechin, and (+)-Catechin.

5. The composition of claim 1 wherein the 3-hydroxyflavan is selected from the group consisting of (−)-Epigallocatechin gallate, (−)-Gallocatechin gallate, (+)-Epigallocatechin gallate, (+)-Gallocatechin gallate, (−)-Epigallocatechin, (−)-Gallocatechin, (+)-Epigallocatechin, and (+)-Gallocatechin.

6. The composition of claim 1 wherein the 3-hydroxyflavan is selected from the group consisting of (−)-Epigallocatechin gallate, (−)-Gallocatechin gallate, (+)-Epigallocatechin gallate and (+)-Gallocatechin gallate.

7. The composition of claim 1 having a pH between 4.0 and 6.0, inclusive.

8. The composition of claim 1 wherein the reducing agent is selected from the group consisting of glutathione and N-acetyl cysteine.

9. A compound having a structure of Formula I

[Chemical structure of Formula I]

Formula I wherein n is independently between 0 and 3, inclusive;
$R_1$ is selected from H, OH, an optionally substituted aryl ester, an optionally substituted aryl thioester, and an optionally substituted aryl amide;
$R_2$ is a reducing agent that is covalently bound via a sulfur atom to the carbon atom of the B-ring;
wherein the reducing agent is selected from the group consisting of a N-substituted cysteine, glutathione, dithiothreitol, dithioerythrol and mercaptoethanol;
with the proviso that where $R_1$ is a substituted aryl ester and n is 2 in the A-ring and n is 3 in the B-ring, then $R_2$ is not glutathione;
with the proviso that where $R_1$ is OH and n is 2, then $R_2$ is not glutathione or glutamine-cysteine dipeptide, or dithiothreitol.

10. The compound of claim 9 wherein the reducing agent is a nutritionally acceptable reducing agent.

11. The compound of claim 9 wherein $R_1$ has a structure according to Formula II

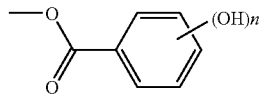

Formula II wherein n is between 0 and 3, inclusive.

12. The compound of claim 9 wherein $R_2$ has a structure according to Formula III

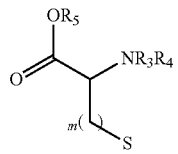

Formula III wherein $R_3$, $R_4$, and $R_5$ are independently selected from the group consisting of H, acyl, acetyl, alkyl, aryl, each of which may be substituted wherein one or both of $R_3$ and $R_4$ other than H, and wherein m is 1.

13. The compound of claim 9 wherein n is independently between 2 and 3, inclusive, $R_1$ is a gallic acid radical, and $R_2$ is a glutathione radical or an N-acetyl cysteine radical.

* * * * *